Feb. 18, 1958 E. S. BOERNER Plant Pat. 1,684
ROSE PLANT
Filed July 11, 1957
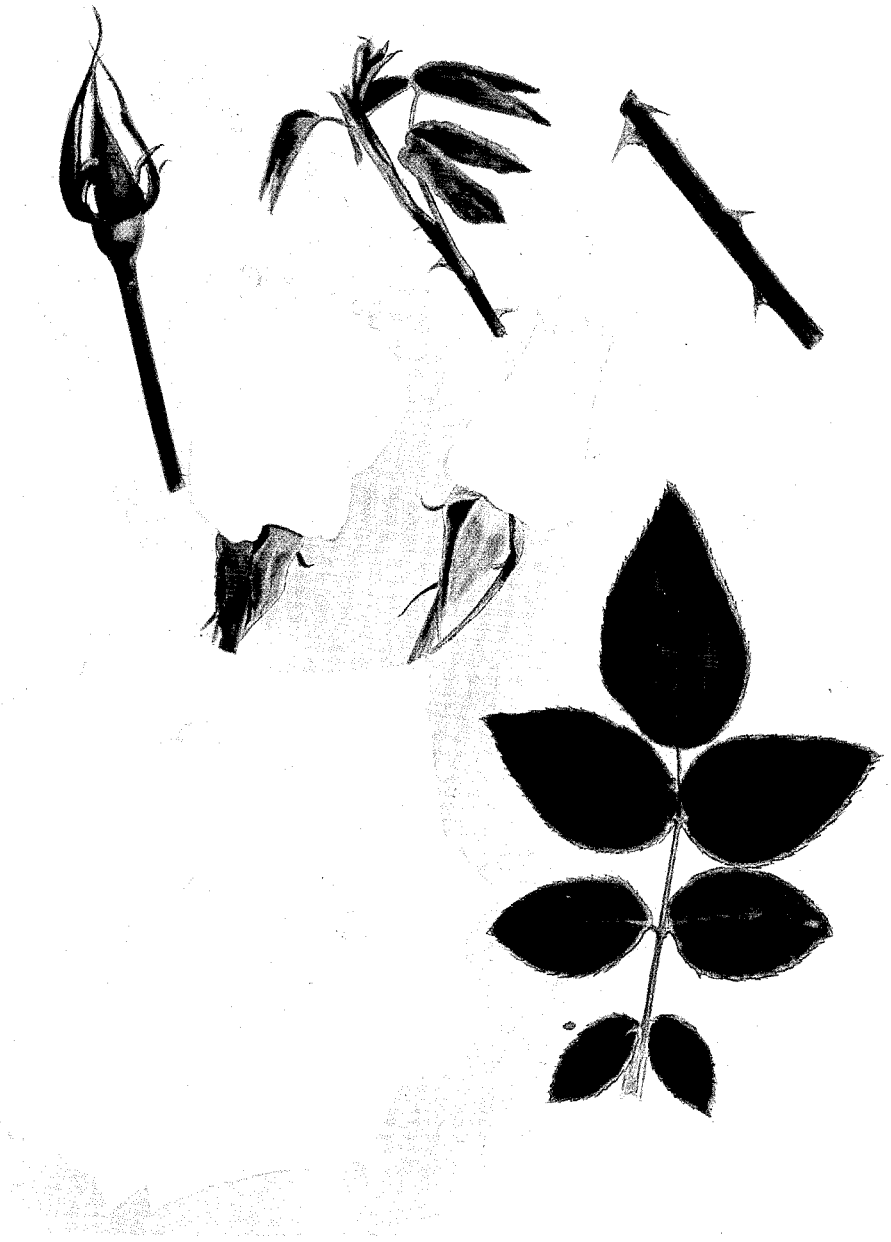
Inventor.
E. S. Boerner
By: Robb & Robb
Attorneys.

United States Patent Office

Plant Pat. 1,684

Patented Feb. 18, 1958

1,684

ROSE PLANT

Eugene S. Boerner, Newark, N. Y., assignor to Jackson & Perkins Company, Newark, N. Y., a corporation of New York Application July 11, 1957, Serial No. 671,368

1 Claim. (Cl. 47—61)

The present invention relates to a new and distinct variety of rose plant of the hybrid tea class, which was originated by me by crossing an unnamed and unpatented seedling of "Eclipse" (Plant Patent No. 172) with the variety "Golden Scepter" (Plant Patent No. 910).

The primary objective of this breeding was to produce a new rose variety comparable to "Eclipse," but in which the flower color is accentuated and the fragrance of the flowers intensified. This objective was fully achieved, along with other improved features, as evidenced by the following characteristics which are outstanding in the new variety and distinguish it from its parents, as well as from all other varieties of which I am aware:

(1) The vigorous habit of plant growth which is more vigorous than that of "Eclipse";

(2) The graceful form of the buds and open flowers;

(3) The Empire Yellow general color tonality of the flowers and the Eugenia Red color of the stamens, the latter being similar to those of "Eclipse"; and (4) The delightful, strong and long-lasting "Old Rose" fragrance of the flowers which is unusual in a yellow rose.

Asexual reproduction of my new variety by budding, as performed at Newark, New York, and also at Pleasanton, California, shows that the aforementioned characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Eclipse."

*Pollen parent.*—"Golden Scepter."

Classification:

*Botanic.*—Hybrid tea.

*Commercial.*—Hybrid tea.

*Flower*

(Observations made from specimens grown outdoors at Newark, New York, in the late morning and near the middle of September.)

Blooming habit: Recurrent—continuous.

Bud:

*Size.*—Large.

*Form.*—Pointed; is not affected by wet or hot weather.

*Color.*—When sepals first divide—Orange, Plate 3. When petals begin to unfurl—Deep Chrome, Plate 3, with outer edges of the petals lightly overcast with Mikado Orange, Plate 3. When half-blown: inside of petals—Light Orange-Yellow, Plate 3, with outer edges of the petals lightly overcast with Mikado Orange, Plate 3; reverse of petals—Buff-Yellow, Plate 4, with edges of petals lightly overcast with Cadmium Yellow, Plate 3.

*Sepals.*—Slightly branched; curl back when petals begin to unfurl. Color: inside—Turtle Green, Plate 32; outside—Bice Green, Plate 17.

*Calyx.*—Color—Bice Green, Plate 17. Shape—apple. Size—large. Aspect—smooth. Odor when rubbed—none.

*Peduncle.* — Length — medium. Aspect — smooth. Strength—erect; heavy. Color—Cerro Green, Plate 5.

*Opening.*—Opens up well; is not affected by adverse weather conditions.

Bloom:

*Size.*—Large. Average size when fully expanded—5 inches.

*Borne.*—Both singly and several together.

*Stems.*—Long; strong.

*Form (when first open).*—High-centered. Permanence—retains its form to the end.

*Petalage.*—Double (full but open center). Number of petals under normal conditions—from 25 to 30.

*Color.*—Center of flower—Empire Yellow, Plate 4. Outer petals—Straw Yellow, Plate 16, lightly overcast with Pinard Yellow, Plate 4. Base of petals (aiglet) — Lemon Chrome, Plate 4. Inside of petals—Empire Yellow, Plate 4, lightly overcast with Pinard Yellow, Plate 4. Reverse of petals—Baryta Yellow, Plate 4. General tonality from a distance—Empire Yellow, Plate 4.

*Discoloration.*—General tonality at end of first day—Empire Yellow, Plate 4. Second day—Empire Yellow, Plate 4, lightly overcast with Pinard Yellow, Plate 4. Third day—Pinard Yellow, Plate 4.

Petals:

*Texture.*—Thick; is not affected by wet or hot weather.

*Appearance.*—Inside—satiny. Outside—shiny.

*Form.*—Oval; slightly notched.

*Arrangement.* — Imbricated (regularly arranged shingle-like).

*Petaloids in center.*—Few; large.

*Persistence.*—Drop off cleanly.

*Fragrance.*—Strong; long-lasting (retained until last petals fall). Nature—"Old Rose perfume" (centifolia).

*Lasting quality.*—On the plant—very long. As cut flower—very long.

*Genital organs*

Stamens, anthers: Large; many; regularly arranged around styles. Color—Deep Chrome, Plate 3.

Stamens, filaments (threads): Long. Color—Eugenia Red, Plate 13.

Pollen: Color—Pale Orange-Yellow, Plate 3.

Styles: Bunched; uneven length; short; thin.

Stigmas: Color—Buff-Yellow, Plate 4.

Ovaries: All enclosed in calyx.

Hips: None.

Seeds: None.

*Plant*

Form: Bush.

Growth: Vigorous; upright.

Foliage: Compound of 5 to 7 leaflets.

*Size.*—Medium.

*Quantity.*—Normal.

*Color.*—New foliage: upper side—Parrot Green, Plate 6, with outer edges Pomegranate Purple. Plate 12; under side—Acajou Red, Plate 13. Old foliage: upper side — Dark, Dull Yellow-Green, Plate 32; under side—Light Elm Green, Plate 17.

*Shape.*—Oval pointed.

*Texture.* — Upper side—leather; glossy. Under side—smooth.

*Ribs and veins.*—Ordinary.

*Edge.*—Serrated (sawtoothed).

*Serration.*—Single; small.

*Leaf stem.*—Color—Rainette Green, Plate 31. Under side—prickly.

*Stipules.*—Medium length; smooth.

Wood:

*New wood.* — Color—Lettuce Green, Plate 5. Bark—smooth.

*Old wood.* — Color — Spinach Green, Plate 5. Bark—smooth.

Thorns:

*Thorns.*—Quantity: on main stalks from base—ordinary; on laterals from stalk — ordinary. Form—narrow base; medium length; hooked downward. Color (when young)—Eugenia Red, Plate 13. Position—irregular.

*Prickles.*—Quantity: on main stalks—none. On laterals—none.

*Short needles.*—Quantity: on main stalks—none. On laterals—none.

I claim:

A new and distinct variety of rose plant of the hybrid tea class, substantially as herein shown and described, characterized particularly as to novelty by the vigorous habit of its plant growth, the graceful form of its buds and open flowers, the Empire Yellow general color tonality of its flowers, combined with the Eugenia Red color of the stamens, and the delightful, strong and long-last fragrance of its flowers.

No references cited.

U. S. DEPARTMENT OF COMMERCE

PATENT OFFICE

CERTIFICATE OF CORRECTION

Plant Patent No. 1,684 February 18, 1958

Eugene S. Boerner

It is hereby certified that error appears in the printed specification of the above numbered patent requiring correction and that the said Letters Patent should read as corrected below.

Column 4, line 16, for "last fragrance" read -- lasting fragrance --.

Signed and sealed this 25th day of March 1958.

(SEAL)
Attest:

KARL H. AXLINE
Attesting Officer

ROBERT C. WATSON
Commissioner of Patents